(12) United States Patent
Chin et al.

(10) Patent No.: US 11,793,643 B2
(45) Date of Patent: *Oct. 24, 2023

(54) METHOD AND APPARATUS FOR CLOSING OFF A PORTION OF A HEART VENTRICLE

(71) Applicant: BioVentrix, Inc., San Ramon, CA (US)

(72) Inventors: Sing-Fatt Chin, Pleasanton, CA (US); Lon S. Annest, Tacoma, WA (US)

(73) Assignee: BioVentrix, Inc., San Ramon, CA (US)

( * ) Notice: Subject to any disclaimer, the term of this patent is extended or adjusted under 35 U.S.C. 154(b) by 341 days.

This patent is subject to a terminal disclaimer.

(21) Appl. No.: 16/816,470

(22) Filed: Mar. 12, 2020

(65) Prior Publication Data

US 2020/0205982 A1 Jul. 2, 2020

Related U.S. Application Data

(60) Continuation of application No. 16/036,689, filed on Jul. 16, 2018, now Pat. No. 10,624,745, which is a
(Continued)

(51) Int. Cl.
*A61F 2/24* (2006.01)
*A61B 17/04* (2006.01)
(Continued)

(52) U.S. Cl.
CPC ........ *A61F 2/2487* (2013.01); *A61B 17/0401* (2013.01); *A61B 17/0469* (2013.01); *A61B 17/06066* (2013.01); *A61B 17/06166* (2013.01); *A61M 25/1011* (2013.01); *A61B 2017/00243* (2013.01); *A61B 2017/0404* (2013.01); *A61B 2017/047* (2013.01);
(Continued)

(58) Field of Classification Search
CPC .......... A61B 17/0401; A61B 17/06066; A61B 17/06166; A61B 2017/00243; A61B 2017/0409; A61B 2017/0435; A61B 2017/047; A61B 2017/06176; A61F 2/2487

See application file for complete search history.

(56) References Cited

U.S. PATENT DOCUMENTS

| | | |
|---|---|---|
| 4,007,743 A | 2/1977 | Blake |
| RE34,021 E | 8/1992 | Mueller et al. |

(Continued)

FOREIGN PATENT DOCUMENTS

| | | |
|---|---|---|
| EP | 1078644 A1 | 2/2001 |
| WO | 00/06028 A1 | 2/2000 |

(Continued)

*Primary Examiner* — Christine H Matthews
(74) *Attorney, Agent, or Firm* — Nixon & Vanderhye P.C.

(57) ABSTRACT

Apparatus and methods to reduce ventricular volume are disclosed. The device takes the form of a transventricular anchor assembly, which presses a portion of the ventricular wall inward, thereby reducing the available volume of the ventricle. The anchor assembly is deployed using a curved introducer that may be inserted into one ventricle, through the septum and into the opposite ventricle. Barbs or protrusions along a tension member of the anchor assembly combined with a mechanical stop and a sealing member hold the device in place once deployed.

20 Claims, 3 Drawing Sheets

Related U.S. Application Data continuation of application No. 14/665,982, filed on Mar. 23, 2015, now Pat. No. 10,022,226, which is a continuation of application No. 12/828,974, filed on Jul. 1, 2010, now Pat. No. 8,986,189, which is a division of application No. 11/450,131, filed on Jun. 8, 2006, now Pat. No. 7,766,816.

(60) Provisional application No. 60/689,012, filed on Jun. 9, 2005.

(51) Int. Cl.
*A61B 17/06* (2006.01)
*A61M 25/10* (2013.01)
*A61B 17/00* (2006.01)
*A61B 17/22* (2006.01)

(52) U.S. Cl.
CPC ........... *A61B 2017/0409* (2013.01); *A61B 2017/0417* (2013.01); *A61B 2017/0435* (2013.01); *A61B 2017/061* (2013.01); *A61B 2017/06028* (2013.01); *A61B 2017/06176* (2013.01); *A61B 2017/22054* (2013.01); *A61B 2017/22067* (2013.01)

(56) References Cited

U.S. PATENT DOCUMENTS

| | | | |
|---|---|---|---|
| 5,295,958 | A | 3/1994 | Shturman |
| 5,766,216 | A | 6/1998 | Gangal et al. |
| 5,800,528 | A | 9/1998 | Lederman et al. |
| 5,830,224 | A | 11/1998 | Cohn et al. |
| 5,853,422 | A | 12/1998 | Huebsch et al. |
| 5,865,791 | A | 2/1999 | Whayne et al. |
| 5,879,366 | A | 3/1999 | Shaw et al. |
| 5,928,250 | A | 7/1999 | Koike et al. |
| 5,961,440 | A | 10/1999 | Schweich, Jr. et al. |
| 6,045,497 | A | 4/2000 | Schweich et al. |
| 6,050,936 | A | 4/2000 | Schweich, Jr. et al. |
| 6,059,715 | A | 5/2000 | Schweich, Jr. et al. |
| 6,125,852 | A | 10/2000 | Stevens et al. |
| 6,155,968 | A | 12/2000 | Wilk |
| 6,162,168 | A | 12/2000 | Schweich, Jr. et al. |
| 6,165,119 | A | 12/2000 | Schweich, Jr. et al. |
| 6,165,120 | A | 12/2000 | Schweich, Jr. et al. |
| 6,171,329 | B1 | 1/2001 | Shaw et al. |
| 6,258,021 | B1 | 7/2001 | Wilk |
| 6,260,552 | B1 | 7/2001 | Mortier et al. |
| 6,406,420 | B1 | 6/2002 | McCarthy et al. |
| 6,494,825 | B1 | 12/2002 | Talpade |
| 6,511,416 | B1 | 1/2003 | Green et al. |
| 6,537,198 | B1 | 3/2003 | Vidlund et al. |
| 6,572,529 | B2 | 6/2003 | Wilk |
| 6,616,684 | B1 | 9/2003 | Vidlund et al. |
| 6,629,921 | B1 | 10/2003 | Schweich et al. |
| 6,705,988 | B2 | 3/2004 | Spence et al. |
| 6,709,382 | B1 | 3/2004 | Horner |
| 6,746,471 | B2 | 6/2004 | Mortier et al. |
| 6,776,754 | B1 | 8/2004 | Wilk |
| 6,808,488 | B2 | 10/2004 | Mortier |
| 6,859,662 | B2 | 2/2005 | Bombardini |
| 6,890,295 | B2 | 5/2005 | Michels et al. |
| 7,146,225 | B2 | 12/2006 | Guenst et al. |
| 7,326,177 | B2 | 2/2008 | Williamson |
| 7,390,329 | B2 | 6/2008 | Westra et al. |
| 7,722,523 | B2 | 5/2010 | Mortier et al. |
| 7,753,923 | B2 | 7/2010 | St. Goar et al. |
| 7,766,816 | B2 | 8/2010 | Chin et al. |
| 7,785,248 | B2 | 8/2010 | Annest et al. |
| 8,066,766 | B2 | 11/2011 | To et al. |
| 8,123,668 | B2 | 2/2012 | Annest et al. |
| 8,394,008 | B2 | 3/2013 | Annest et al. |
| 8,425,402 | B2 | 4/2013 | Annest et al. |
| 8,449,442 | B2 | 5/2013 | Annest et al. |
| 8,491,455 | B2 | 7/2013 | Annest et al. |
| 8,506,474 | B2 | 8/2013 | Chin et al. |
| 8,636,639 | B2 | 1/2014 | Annest et al. |
| 8,986,189 | B2 | 3/2015 | Chin et al. |
| 10,022,226 | B2 | 7/2018 | Chin et al. |
| 11,478,353 | B2 * | 10/2022 | Van Bladel ........... A61F 2/2481 |
| 2001/0041821 | A1 | 11/2001 | Wilk |
| 2002/0058855 | A1 | 5/2002 | Schweich, Jr. et al. |
| 2002/0077524 | A1 | 6/2002 | Schweich, Jr. et al. |
| 2002/0120298 | A1 | 8/2002 | Kramer et al. |
| 2002/0123768 | A1 | 9/2002 | Gilkerson et al. |
| 2002/0169359 | A1 | 11/2002 | McCarthy et al. |
| 2002/0169360 | A1 | 11/2002 | Taylor et al. |
| 2002/0188170 | A1 | 12/2002 | Santamore et al. |
| 2003/0032979 | A1 | 2/2003 | Mortier et al. |
| 2003/0102000 | A1 | 6/2003 | Stevens et al. |
| 2003/0163165 | A1 | 8/2003 | Bornzin et al. |
| 2003/0166992 | A1 | 9/2003 | Schweich, Jr. et al. |
| 2003/0181951 | A1 | 9/2003 | Cates |
| 2004/0167580 | A1 | 8/2004 | Mann et al. |
| 2004/0225304 | A1 | 11/2004 | Vidlund et al. |
| 2005/0065506 | A1 | 3/2005 | Phan |
| 2005/0096498 | A1 | 5/2005 | Houser et al. |
| 2005/0137688 | A1 | 6/2005 | Salahieh et al. |
| 2005/0143620 | A1 | 6/2005 | Mortier et al. |
| 2005/0288613 | A1 | 12/2005 | Heil, Jr. |
| 2006/0009800 | A1 | 1/2006 | Christianson |
| 2006/0135962 | A1 | 6/2006 | Kick et al. |
| 2006/0131238 | A1 | 7/2006 | Hall |
| 2006/0161040 | A1 | 7/2006 | McCarthy et al. |
| 2006/0161238 | A1 | 7/2006 | Hall |
| 2006/0200002 | A1 | 9/2006 | Guenst |
| 2006/0241340 | A1 | 10/2006 | Schroeder et al. |
| 2006/0247672 | A1 | 11/2006 | Vidlund et al. |
| 2006/0276684 | A1 | 12/2006 | Speziali |
| 2007/0010876 | A1 | 1/2007 | Salahieh et al. |
| 2007/0049971 | A1 | 3/2007 | Chin et al. |
| 2007/0055303 | A1 | 3/2007 | Vidlund et al. |
| 2007/0073274 | A1 | 3/2007 | Chin et al. |
| 2007/0112244 | A1 | 5/2007 | McCarthy et al. |
| 2007/0161846 | A1 | 7/2007 | Nikotic et al. |
| 2007/0203503 | A1 | 8/2007 | Salahieh et al. |
| 2008/0082132 | A1 | 4/2008 | Annest et al. |
| 2008/0097148 | A1 | 4/2008 | Chin et al. |
| 2008/0269551 | A1 | 10/2008 | Annest et al. |
| 2008/0294251 | A1 | 11/2008 | Annest et al. |
| 2009/0093670 | A1 | 4/2009 | Annest et al. |
| 2009/0270980 | A1 | 10/2009 | Schroeder et al. |
| 2010/0010538 | A1 | 1/2010 | Juravic et al. |
| 2010/0016655 | A1 | 1/2010 | Annest et al. |
| 2010/0057000 | A1 | 3/2010 | Melsheimer et al. |
| 2011/0160750 | A1 | 6/2011 | Annest et al. |
| 2012/0190958 | A1 | 7/2012 | Annest et al. |
| 2013/0090523 | A1 | 4/2013 | Van Bladel et al. |
| 2013/0090672 | A1 | 4/2013 | Butler et al. |
| 2013/0096579 | A1 | 4/2013 | Annest et al. |
| 2013/0324787 | A1 | 12/2013 | Chin et al. |
| 2013/0325041 | A1 | 12/2013 | Annest et al. |
| 2014/0031613 | A1 | 1/2014 | Annest et al. |
| 2014/0051916 | A1 | 2/2014 | Chin et al. |

FOREIGN PATENT DOCUMENTS

| | | |
|---|---|---|
| WO | 2002/30335 A2 | 4/2002 |
| WO | 2003/032818 A3 | 4/2003 |
| WO | 2005/092203 A1 | 10/2005 |
| WO | 2006/044467 A2 | 4/2006 |
| WO | 2007/022519 A2 | 2/2007 |

* cited by examiner

METHOD AND APPARATUS FOR CLOSING OFF A PORTION OF A HEART VENTRICLE

CROSS-REFERENCES TO RELATED APPLICATIONS

The present application is a continuation of U.S. patent application Ser. No. 16/036,689 filed Jul. 16, 2018, which is a continuation of U.S. patent application Ser. No. 14/665,982 filed Mar. 23, 2015, now U.S. Pat. No. 10,022,226, which is a continuation of U.S. Ser. No. 12/828,974 filed on Jul. 1, 2010, now U.S. Pat. No. 8,986,189, which is a divisional of U.S. Ser. No. 11/450,131 filed Jun. 8, 2006, now U.S. Pat. No. 7,766,816, which claims the benefit of U.S. Provisional Application No. 60/689,012 filed Jun. 9, 2005; the full disclosures of which are incorporated herein by reference in their entirety.

FIELD OF THE INVENTION

The present invention relates to methods and apparatus for temporarily or permanently closing off a portion of the ventricle of the heart.

BACKGROUND OF THE INVENTION

In left ventricular hypertrophy, the myocardium of the left ventricle becomes thickened to the point of interfering with effective heart contraction. A surgical procedure for treating congestive heart failure, involves removing a triangular portion of a patient's heart. In this operation, approximately one-third of the patient's left ventricular muscle is removed. The result is that the smaller heart pumps more efficiently. This new technique of course requires open-heart surgery, with its attendant expense and extended convalescence.

One method to reduce ventricular volume is disclosed in U.S. Pat. No. 6,776,754 to Wilk, which is hereby incorporated by reference in its entirety.

For this and other potential procedures, it would be beneficial to have a method and system that could be temporarily and/or permanently implanted to close off a portion of the ventricle.

SUMMARY OF THE INVENTION

The present invention relates to a catheter or surgical based system capable of closing off a portion of a ventricle of a patient. The ventricle may be temporarily blocked during a surgical procedure or it may be permanently or semi-permanently closed off to improve cardiac function.

The present invention takes the form of an anchor for performing heart reconstruction including an elongated body, a plurality of protrusions extending from the body, and first and second mechanical stops or sealing members attachable to the body.

The anchor of mechanical stop may include two or more folding arms. The folding arms may be pivotally attached to the first end of the body.

One end of the anchor may include a curved needle that forms one end of the anchor.

The anchor may be used with a curved introducer. The elongated body being sized and configured to pass through the curved introducer.

The second sealing member may be held in place by a plurality of protrusions.

The sealing member may be formed of a resilient material.

A method of performing ventricular reconstruction, including the steps: (a) passing a curved needle through an anterior wall of a left ventricle of a patient; (b) passing the curved needle through the septum and into the right ventricle; (c) inserting an anchor into the needle; (d) allowing one or more arms located on a distal end of said anchor to deploy; (e) removing the curved needle; (f) placing a sealing member over a proximal end of said anchor; (g) folding a wall of the ventricle inward; (h) and using the sealing member to hold the folded wall in place.

The method may include passing the curved needle through an anterior wall of the right ventricle prior to step (d).

The method may be used to reduce the volume of the left ventricle and/or to treat left ventricular hypertrophy.

The method may include using the sealing member to hold the wall of the ventricle in place by engaging one or more protrusions extending from the anchor.

The method using a sealing member formed of a resilient material, such that the sealing member is resiliently deformed, thereby resiliently pressing against the wall of the ventricle.

The method may include the step of removing a portion of the anchor after the wall of the ventricle has been moved.

The method may be used to temporarily or permanently implant the device.

DETAILED DESCRIPTION OF THE INVENTION

Figure 1A:
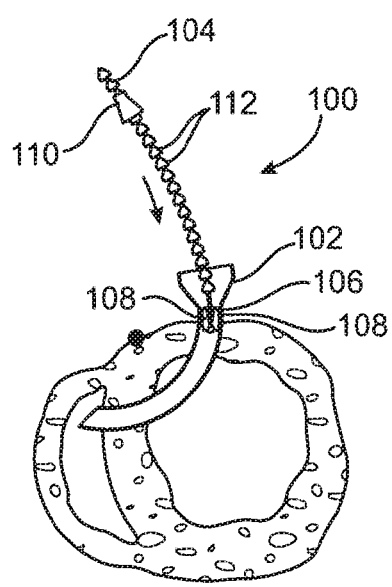
FIGS. 1A-1C show a method and device for left ventricular reconstruction using a left ventricular approach.
Figure 1B:
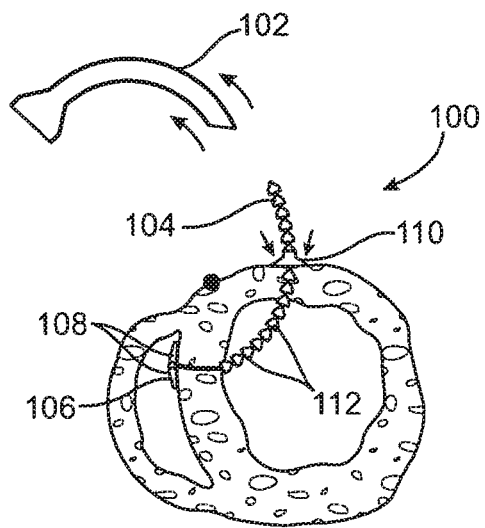
Figure 1C:
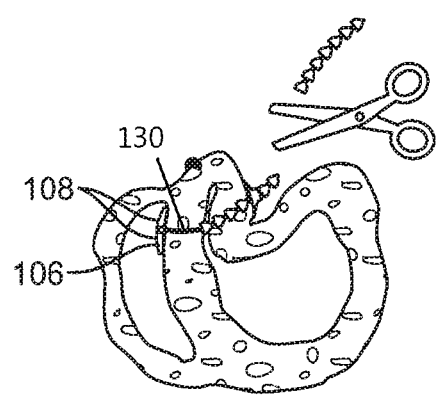

FIGS. 1A-1C show a method and device 100 for left ventricular reconstruction using a left ventricular approach. The device is an anchor deployment system 100, which is guided to the correct location on the heart by introducing a hollow curved introducer or needle 102 in through the anterior wall of the left ventricle. A visual guidance system, such as TEE, may be used to ensure the placement accuracy. The tip of the curved needle 102 is then guided through the septum and into the right ventricle. Either before placement or once the needle 102 is in place, the transventricular anchor assembly 104 is loaded into the needle 102. The distal tip of the anchor assembly 104 is extended into the cavity of the right ventricle.

The distal tip of the anchor assembly 104 has a mechanical stop 106, also referred to as a distal anchor. Although it may take any suitable form, such as a resilient member or mechanical device, in the embodiment shown, the stop 106 has two or more pivoting arms 108. While the anchor assembly 104 is within the needle 102, the arms 108 are held close to the body of the anchor assembly 104. When the distal tip of the anchor assembly 104 extends beyond the distal tip of the needle 102, the arms 108 are free to open. The arms 108 may be biased toward the open position or they maybe be manually opened. Once opened, the arms 108 prevent the distal end of the anchor assembly 104 from passing back through the opening in the septum.

After the anchor assembly 104 is in place, the needle 102 may be removed. A proximal sealing lock 110, also referred to as a proximal anchor, is then slid onto the proximal end of the anchor assembly 104. The sealing lock 110 is slid along a tension member 130 of the anchor assembly and over one or more barbs 112 or other protrusions extending from the body of the anchor assembly 104. The barbs 112 may take any suitable form, such as rounded or triangular. In the embodiment shown, the barbs 112 are generally triangular in shape. The proximal sealing lock 110 is advance until the anterior wall of the left ventricle is pressed inward, thereby folding the wall and reducing the interior volume of the left ventricle. Once the sealing lock 110 is advanced into place, the proximal portion of the tension member of the anchor assembly 104 may be trimmed or cut off Although the sealing lock 110 may be formed of any suitable material, the sealing lock 110 shown is made of a resilient material to allow it open and be compressed against the heart tissue. The resilience of the material provides benefits both in helping to seal the opening created as well has resiliently holding the wall of the ventricle in the modified configuration.

In alternate embodiments, an adhesive, bonding or other mechanical or chemical means may be used to connect the sealing lock 110 to the anchor assembly 104.

If desired, the tip of the hollow needle 102 may be equipped with a pressure sensor to guide the practitioner to know if the tip is in the left ventricle, septum or the right ventricle by sensing the pressure. The hollow needle 102 may also be equipped with electrical sensor (EKG, Monophasic Action Potential) to sense if the puncture sight is the viable tissue or infracted tissue.

Figure 2A:
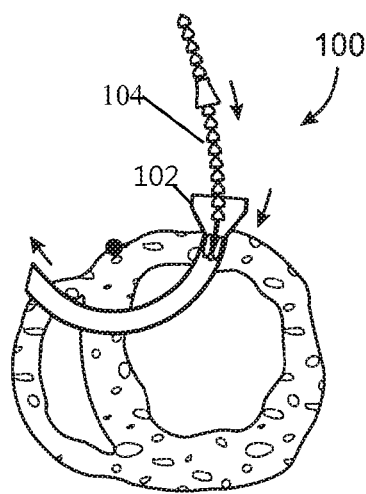
FIGS. 2A-C show an alternate procedure of FIGS. 1A-C.
Figure 2B:
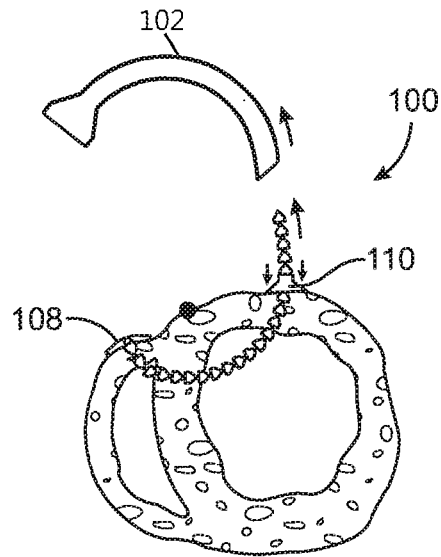
Figure 2C:
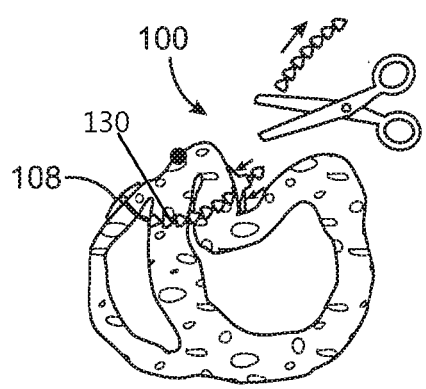

FIGS. 2A-C show an alternate procedure of that shown in FIGS. 1A-C. In this method, the distal end of the anchor is again guided to the anterior wall of the left ventricle. The tip of the needle 102 is then guided through the septum and into the right ventricle. In the configuration shown in FIG. 2A, the needle 102 also extends through the anterior wall of the right ventricle. Once deployed, the distal tip of the anchor assembly 104 is outside the right ventricle and the proximal tip is outside the left ventricle.

Figure 3A:
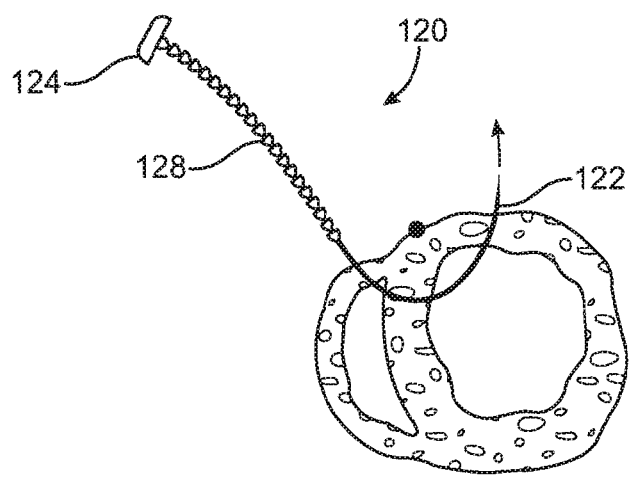
FIGS. 3A-B show a method and device for left ventricular reconstruction using a right ventricular approach.
Figure 3B:
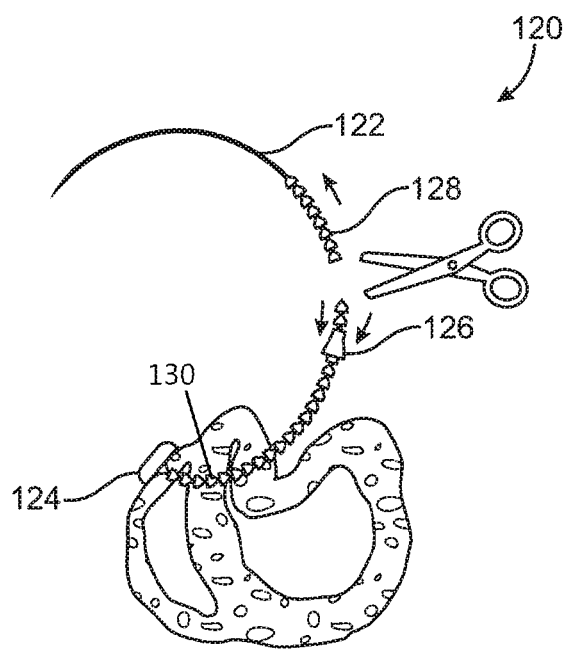

FIGS. 3A-B show a method and device for left ventricular reconstruction using a right ventricular approach. In this version, a curved needle 122 forms the distal tip of the anchor assembly 120. The curved needle 122 is inserted through the anterior wall and into the right ventricle, through the septum, and through the anterior wall of the left ventricle. The tension member 130 of the anchor assembly 120 follows the curved needle 122 and is fed through until the proximal stop 124 engages the anterior surface of the right ventricle. The anterior wall of the left ventricle is pressed inward over the body of the anchor assembly. A distal sealing stop 126 is threaded over the anchor assembly 120 and slid in place against the anterior surface of the right ventricle. The heart tissue may be pressed inward to fold the wall of the heart prior to the placement of the sealing stop 126 or the sealing stop 126 may be used to manipulate the heart tissue. A plurality of barbs or protrusions 128 extend from the surface of the tension member 130. The barbs 128 help hold the heart tissue in place. The curved needle 122 and the excess portion of the distal end of the anchor assembly may be removed. This may be done before or after the distal sealing stop 126 has been placed.

The transventricular anchor may be temporarily or permanently implanted. A temporary implantation may be beneficial to test the effectiveness of the treatment for a particular patient. Other surgical procedures may only require a temporary reduction in ventricle volume. For these situations, the device may be removable. To remove the device, it may be cut or broken or another release mechanism may be used to allow for removal of the device. Once the efficacy is confirmed for a patient, a permanent version of the anchor could be implanted. Alternately, a semipermanent or permanent device may be implanted initially.

The transventricular anchor may be used to treat medical conditions including left ventricular hypertrophy. While the examples given are specific to performance of reconfiguration of the left ventricle. Other procedures could also be performed to reduce the internal volume of other bodily structures, including other chambers of the heart, gastric system, etc.

The present invention may be deployed during an open-heart procedure or it may be one using minimally invasive techniques using catheter systems and/or ports formed between the ribs. With reference to FIGS. 1(A) to 1(C) and 2(A) to 2(C), the invention may be embodied as a system for performing ventricular reconstruction of a heart, the method comprising: an elongate body, such as a needle 102, that is configured for insertion into the heart so that a distal end of the elongate body is positioned in a right ventricle of the heart; an anchor, such as mechanical stop 106, that is configured for delivery into the right ventricle of the heart via the elongate body and that is configured to engage the septum when the mechanical stop is positioned in the right ventricle; a tension member 130 that is coupled with the mechanical stop 106, so that tension applied to the tension member is transferred to the mechanical stop and to the septum when the mechanical stop is engaged with the septum, wherein the tension member has a sufficient length such that the tension member extends through the wall and septum of the heart and to an exterior of a patient's body while the mechanical stop is engaged with the septum; and a proximal anchor, such as a sealing lock 110, and having a central aperture through which the tension member is insertable to couple the proximal anchor with the tension member, the proximal anchor being configured to move distally along the tension member toward the mechanical stop and being configured to prevent proximal movement of the proximal anchor along the tension member away from the mechanical stop; wherein the proximal anchor is configured to engage the wall of the heart to enable the wall to be biased toward engagement with the septum.

Many features have been listed with particular configurations, options, and embodiments. Anyone or more of the features described may be added to or combined with any of the other embodiments or other standard devices to create alternate combinations and embodiments.

Although the invention has been fully described above, in relation to various exemplary embodiments, various additions or other changes may be made to the described embodiments without departing from the scope of the present invention. Thus, the foregoing description has been provided for exemplary purposes only and should not be interpreted to limit the scope of the invention.

What is claimed is:

1. An anchor device for treating a heart within a patient comprising:
   a tension member;
   a proximal anchor attached to a proximal end of the tension member;
   a needle attached to a distal end of the tension member, the needle including a tissue penetrating tip configured to penetrate through external walls of the heart and be moved out of the heart; and
   a second anchor configured to be slidably attached to the tension member;
   wherein the tension member is configured to be tensioned after the needle penetrates the external walls of the heart to advance the second anchor along at least a portion of the length of the tension member into engagement with one of the external walls of the heart.

2. The anchor device of claim 1, wherein the needle has a curved or arcuate configuration and wherein the needle is made of a more rigid material than the tension member.

3. The anchor device of claim 1, wherein the needle is configured to be removable from the tension member after the tension member penetrates through the external walls of the heart.

4. The anchor device of claim 1, wherein the proximal anchor is axially affixed and pivotably coupled to the tension member.

5. The anchor device of claim 4, wherein the proximal anchor includes two or more arms.

6. A anchor device for treating a heart within a patient comprising:
 a tension member;
 an anchor attached to a proximal end of the tension member;
 a needle attached to a distal end of the tension member, the needle including a tissue penetrating tip that is configured for penetrating through external walls of the heart; and
 an additional anchor configured to be removably couple-able with the distal end of the tension member and slidable proximally along the tension member to engage an opposing external wall of the external walls of the heart to close a lower portion of the heart,
 wherein the tension member couples the needle and the anchor, and the tension member is configured to be tensioned after the needle penetrates through the external walls of the heart to advance the anchor into engagement with one of the external walls of the heart.

7. The anchor device of claim 6, wherein the tension member includes a plurality of protrusions that extend from a body of the tension member, and wherein the additional anchor is held in place by the plurality of protrusions.

8. The anchor device of claim 7, wherein the plurality of protrusions are configured to engage heart tissue and hold the heart tissue in place.

9. The anchor device of claim 6, wherein the additional anchor is slidable proximally along the tension member in a one way direction.

10. A method for applying an anchor to a heart comprising:
 penetrating external walls of the heart via a needle of an anchor device, the anchor device further comprising a tension member and an anchor attached to a proximal end of the tension member, wherein the needle is attached to a distal end of the tension member;
 pulling the needle through the external walls of the heart to advance the anchor, via the tension member, toward the heart; and
 engaging a first external wall of the external walls of the heart with the anchor.

11. The method of claim 10, wherein the needle has a curved or arcuate configuration.

12. The method of claim 10, wherein the anchor of the anchor device is pivotably coupled to the proximal end of the tension member.

13. The method of claim 10, wherein the anchor includes two or more arms.

14. The method of claim 10, wherein the anchor is a first anchor and wherein the method further comprises:
 coupling a second anchor with the distal end of the tension member;
 sliding the second anchor proximally along the tension member into engagement with a second external wall of the external walls which opposes the first external wall of the heart; and
 applying tension to the first and second anchors, via the tension member, to bring the first external wall and the second external wall into apposition.

15. The method of claim 14, further comprising removing the needle prior to coupling the second anchor with the distal end of the tension member.

16. The method of claim 14, further comprising removing the needle subsequent to coupling the second anchor with the distal end of the tension member.

17. The method of claim 14, wherein the second anchor is slidable proximally along the tension member in a one way direction.

18. The method of claim 14, wherein the tension member includes a plurality of protrusions that extend from a body of the tension member, and wherein the second anchor is held in place by the plurality of protrusions.

19. The method of claim 18, further comprising engaging heart tissue with the plurality of protrusions to hold the heart tissue in place via the plurality of protrusions.

20. The method of claim 10, wherein penetrating the external walls of the heart comprises penetrating external walls of an apex of the heart.

* * * * *